(12) United States Patent
Boghosian

(10) Patent No.: US 10,231,805 B2
(45) Date of Patent: Mar. 19, 2019

(54) METHOD OF PREPARING DENTITION FOR THE TAKING OF A DENTAL IMPRESSION

(71) Applicant: Alan Ara Boghosian, Glenview, IL (US)

(72) Inventor: Alan Ara Boghosian, Glenview, IL (US)

(*) Notice: Subject to any disclaimer, the term of this patent is extended or adjusted under 35 U.S.C. 154(b) by 156 days.

(21) Appl. No.: 15/368,874

(22) Filed: Dec. 5, 2016

(65) Prior Publication Data
US 2017/0079753 A1 Mar. 23, 2017

Related U.S. Application Data

(63) Continuation-in-part of application No. 11/153,132, filed on Jun. 15, 2005, now abandoned.

(51) Int. Cl.
*A61C 9/00* (2006.01)
*A61K 6/10* (2006.01)

(52) U.S. Cl.
CPC . *A61C 9/00* (2013.01); *A61K 6/10* (2013.01)

(58) Field of Classification Search
CPC .................................. A61C 9/00; A61K 6/10
See application file for complete search history.

(56) References Cited

U.S. PATENT DOCUMENTS

| | | |
|---|---|---|
| 3,874,905 A | 4/1975 | Knights |
| 3,937,807 A | 2/1976 | Haefele |
| 3,959,458 A | 5/1976 | Agricola et al. |
| 4,051,234 A | 9/1977 | Gieske et al. |
| 4,395,398 A | 7/1983 | Yamamoto et al. |
| 4,617,950 A | 10/1986 | Porteous et al. |
| 4,657,959 A | 4/1987 | Bryan et al. |
| 4,691,039 A | 9/1987 | Aasen et al. |

(Continued)

FOREIGN PATENT DOCUMENTS

| | | |
|---|---|---|
| DE | 4129613 A1 | 3/1993 |
| EP | 1188419 A2 | 3/2002 |

OTHER PUBLICATIONS

Millar, et al., The effect of a surface wetting agent on void formation in impressions, Journal of Prosthetic Dentistry, vol. 77, 1997, pp. 54-56.

(Continued)

*Primary Examiner* — Heidi M Eide
(74) *Attorney, Agent, or Firm* — McNees Wallace & Nurick LLC

(57) ABSTRACT

A method of taking a dental impression of dentition including conditioning a surface comprising one or more of dentition and a dental appliance by the application thereto of a wetting agent to form a controlled hydrophilic wet film. The wetting agent includes water, a surfactant, a compatibilizing agent and a film stabilizing agent. The controlled hydrophilic wet film is hydrophilic and is formed by brushing the wetting agent onto the dentition. The brushing controls the thickness and hydrophilicity of the controlled hydrophilic film to a thickness and hydrophilicity that is capable of inducing flow of an impression material that comes into contact with the controlled hydrophilic film. The flow is sufficient to flow into sub-gingival places. The film is contacted with a dental impression material selected from the group consisting of hydrophilic and hydrophobic dental impression materials.

22 Claims, 2 Drawing Sheets

(56) References Cited

U.S. PATENT DOCUMENTS

| | | | |
|---|---|---|---|
| 4,752,633 A | 6/1988 | Aasen et al. | |
| 4,778,832 A | 10/1988 | Futami et al. | |
| 5,534,560 A | 7/1996 | Busin et al. | |
| 5,554,028 A | 9/1996 | Hare et al. | |
| 5,830,951 A | 11/1998 | Fiedler | |
| 5,863,965 A | 1/1999 | Hare | |
| 6,536,448 B2 * | 3/2003 | McDevitt | A61C 15/041 |
| | | | 132/321 |
| 6,783,746 B1 | 8/2004 | Zhang et al. | |
| 2002/0071813 A1 | 6/2002 | Angeletakis et al. | |
| 2005/0084460 A1 | 4/2005 | Winston et al. | |
| 2005/0123592 A1 | 6/2005 | Gyurik et al. | |
| 2008/0003538 A1 * | 1/2008 | Wittrock | A61C 9/0033 |
| | | | 433/136 |

OTHER PUBLICATIONS

Millar, et al. An in vivo study of a clinical surfactant used with poly(vinyl siloxane) impression materials, Quintessence International, vol. 27, No. 10, 1996, pp. 707-709.
International Search Report, PCT/US2005/021157.

* cited by examiner

METHOD OF PREPARING DENTITION FOR THE TAKING OF A DENTAL IMPRESSION

CROSS-REFERENCE TO RELATED APPLICATIONS

This patent application is a continuation-in-part of U.S. patent application Ser. No. 11/153,132 filed on Jun. 15, 2005, and entitled "Method of preparing dentition for the taking of a dental impression", the disclosure of which is hereby incorporated by reference herein in its entirety and made part of the present U.S. utility patent application for all purposes.

TECHNICAL FIELD

The present invention generally relates to the taking of dental impressions. More particularly, the invention relates to the conditioning of dentition substantially immediately prior to the taking of the dental impression to wet-out the dentition. More specifically the invention relates to the application of a wetting agent, a surface treating agent or other impression preparatory agent to the dentition prior to the taking of a dental impression when using a vinyl polysiloxane, silicone or other rubber or elastomeric impression material. The inventive material may also include hemostatic materials or functional silicone polymers that can co-polymerize with the tray (impression) material.

BACKGROUND OF THE INVENTION

It is known to apply a wetting agent to a tooth preparation prior to the taking of an impression with hydrocolloid impression materials, such as polyethers. In recent years the use of hydrocolloids has decreased in favor of vinyl polysiloxane, silicone or other rubber or elastomeric impression materials. A drawback to the use of these dental impression materials has been their hydrophobicity, making it difficult to take precise impressions of the details of the tooth and/or hard tissue when it is wetted with blood, saliva, or other fluids. When making the impression, the blood, saliva, or other fluids are forced into the margins of the teeth or pits and fissures in the teeth by the hydrophobic silicone impression material, rendering it difficult to take detailed and precise impressions because of the high surface tension of the materials. The dental practitioner may attempt to dry the oral cavity by blowing air into the oral cavity, but this is cumbersome not only for the practitioner but also the patient, particularly where the patient is bleeding. The hydrophobicity of dental impression materials also prevents the formation of accurate models formed from gypsum slurries.

Repeated attempts have been made to render silicone dental impression materials more hydrophilic by including various ionic or non-ionic surfactants in the composition, as is described, for example, in DE 4129613 to Hefner et al., U.S. Pat. No. 4,657,959 to Bryan et al., U.S. Pat. No. 4,691,039 to Aasen et al., and U.S. Pat. No. 4,752,633 to Aasen et al. U.S. Pat. No. 4,778,832 to Futami discloses use of a protein additive, such as albumin, as well as a silicone oil or non-ionic surfactant to increase hydrophilicity. While these materials have met with some success, the additives sometimes suffer from certain drawbacks, including instability in moist air, deactivation of platinum catalyst complexes, and reduction in the tear strength of the dental impression. For example, they may swell first in water, and then dissolve gradually, and undergo phase separation, such as in vinyl-termimated polydimethylsiloxane base components.

U.S. Pat. No. 5,534,560 describes an attempt to modify the impression material rather than wetting the dentition. As such, this patent describes a variation of the prior art that involves changing the chemistry of the impression material to make it less hydrophobic.

A need exists therefore, for a method of preparing or conditioning dentition to receive or physically contact a dental impression material in order to affect a detailed and accurate impression. That is, the need exists for a material that will wet the dentition as opposed to modifying the impression material. The method should be useful with both hydrophobic and hydrophilic dental impression materials. The method should also be useful in assisting the practitioner in removing the impression material from the dentition.

SUMMARY OF THE INVENTION

In general, a method of conditioning dentition before the taking of a dental impression includes the step of applying a wetting agent, a surface treating agent or other impression preparatory agent to the dentition. The wetting agent may include a surfactant or surfactant-like molecule, compound, composition or mixture with a dentally suitable carrier. The wetting agent may also include a hemostatic or vasoconstrictor agent or functional silicone polymers that can co-polymerize with the tray (impression) material. All such materials shall be collectively referred to herein as "wetting agent" or "wetting agents" or the like unless otherwise specified.

In one embodiment, the present disclosure includes a method of taking a dental impression of dentition. The method includes conditioning a surface, the surface being one or more of dentition and a dental appliance by the application thereto of a wetting agent to form a controlled hydrophilic wet film. The wetting agent includes water, a surfactant, a compatibilizing agent and a film stabilizing agent. The controlled hydrophilic wet film is hydrophilic and is formed by brushing the wetting agent onto the dentition. The brushing controls the thickness and hydrophilicity of the controlled hydrophilic film to a thickness and hydrophilicity that is capable of inducing flow of an impression material that comes into contact with the controlled hydrophilic film. The flow is sufficient to flow into sub-gingival places. The film on the one or more of dentition and a dental appliance is contacted with a dental impression material selected from the group consisting of hydrophilic and hydrophobic dental impression materials. The film stabilizing agent includes glycerin or polyethylene glycol. "Dental appliance", as used herein, includes any intraoral surface other than dentition, such as, but not limited to, restorative materials, implant impression coping, bridges or prosthetics.

In another embodiment, the present disclosure includes a method of taking a dental impression of dentition. The method includes conditioning a surface being one or more of dentition and a dental appliance by the application thereto of a wetting agent to form a controlled hydrophilic wet film. The controlled hydrophilic wet film is formed by brushing the wetting agent onto the dentition. The brushing controls the thickness and hydrophilicity of the controlled hydrophilic film to a thickness and hydrophilicity that is capable of inducing flow of an impression material that comes into contact with the controlled hydrophilic film. The flow induced is sufficient to flow into sub-gingival places. The film is contacted with a dental impression material selected from the group consisting of hydrophilic and hydrophobic dental impression materials. The wetting agent comprises a surfactant and a carrier. The carrier is a water soluble composition including glycerin. The conditioning includes rendering the surface of the one or more of dentition and a dental appliance surface hydrophilic.

In another embodiment, the present disclosure includes a method of taking a dental impression of dentition. The method includes conditioning a surface being one or more of dentition and a dental appliance by the application thereto of a wetting agent to form a controlled hydrophilic wet film. The controlled hydrophilic wet film is formed by brushing the wetting agent onto the dentition. The brushing controls the thickness and hydrophilicity of the controlled hydrophilic film to a thickness and hydrophilicity that is capable of inducing flow of an impression material that comes into contact with the controlled hydrophilic film. The flow induced is sufficient to flow into sub-gingival places. The film is contacted with a dental impression material selected from the group consisting of hydrophilic and hydrophobic dental impression materials. The wetting agent comprises a surfactant and a carrier. The carrier is a water soluble composition including polyethylene glycol. The conditioning includes rendering the surface of the one or more of dentition and a dental appliance surface hydrophilic.

In another embodiment, the present disclosure includes a method of taking a dental impression of dentition. The method includes preparing the dentition with a gingival retraction cord. The gingival retraction cord is contacted with a wetting agent. The wetting agent includes water, a surfactant, a compatibilizing agent, and a film stabilizing agent. The preparing includes conditioning the dentition by the application thereto of the wetting agent by one or both of the gingival retraction cord and brushing to form a controlled hydrophilic wet film. The conditioning controls the thickness and hydrophilicity of the controlled hydrophilic film to a thickness and hydrophilicity that is capable of inducing flow of an impression material that comes into contact with the controlled hydrophilic film. The induced flow is sufficient to flow into sub-gingival places. The method further includes contacting the dentition with a dental impression material.

A method of taking a dental impression includes the step of applying such a wetting agent to the dentition before contacting the dentition with a vinyl polysiloxane, silicone or other rubber or elastomeric impression material. The impression material may be hydrophobic or hydrophilic.

PREFERRED EMBODIMENTS FOR CARRYING OUT THE INVENTION

Figure 1:
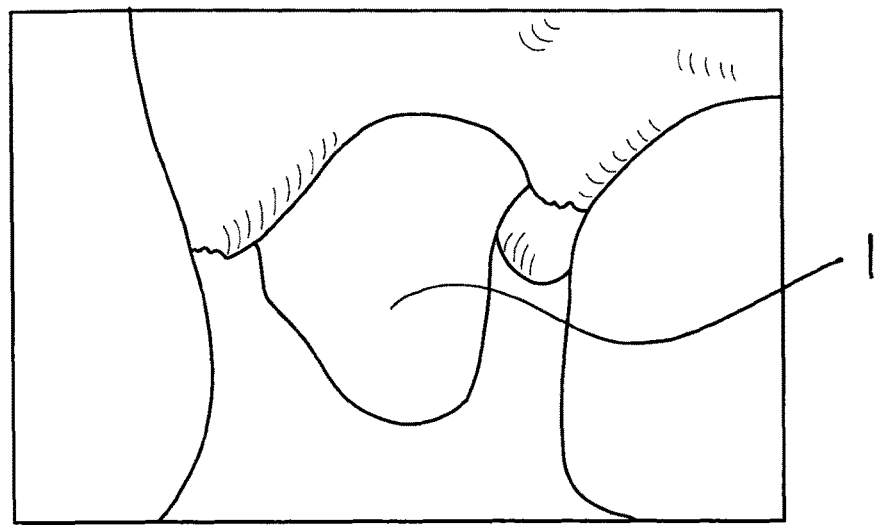
FIG. 1 is an elevational view of a prepared tooth.

The present invention provides a method of taking a dental impression that includes conditioning the dentition of which it is desired to make an impression. The inventive method includes applying a wetting agent, such as a surfactant-containing composition, to the dentition or dental appliance and then applying the impression material. The invention has usefulness with any dental impression material, but is particularly suitable for use with vinyl polysiloxane and silicone or other rubber or elastomeric impression materials or water-based materials, such as alginate or hydrocolloid based impression materials. The invention has an additional particular usefulness with hydrophilic dental impression materials but is suitable for use with hydrophobic materials as well.

Conditioning the surface includes forming a controlled hydrophilic film. The conditioning includes an application method that includes brushing. Brushing, according to the present disclosure, results in the distribution of the wetting agent in a manner that provides a controlled hydrophilic film that facilitates subsequently applied impression material flow. "Controlled hydrophilic film", as utilized herein, means a film or coating that is formed on dentition or a dental appliance surface in a controlled, clinically acceptable manner that renders the surface hydrophilic across the surface intended to be covered with impression material. In addition, the controlled hydrophilic film imparts a high degree of flow of impression material on the surface to permit, for example, in some embodiments, flow into sub-gingival spaces. In addition, the controlled hydrophilic film includes the property of providing little or no interference with the reproduction of detail of the impression material. The brushing controls the thickness and hydrophilicity of the controlled hydrophilic film to a thickness and hydrophilicity that is capable of inducing flow of an impression material that comes into contact with the controlled hydrophilic film.

The wetting agent includes a combination of ingredients that permits the formation of a controlled hydrophilic film upon the application by brushing. The wetting agent includes water, a surfactant, a compatibilizing agent and a film stabilizing agent.

The surfactant in the wetting agent includes a surfactant or a surfactant-like material, all such materials referred to as "surfactants" unless otherwise noted. By "surfactant" and "surfactant-like" it is meant any material that serves to reduce liquid-to-liquid surface tension. The surfactant should be suitable for use in the oral cavity, such as Igepal co-530, a nonyl phenoxy-poly (ethyleneoxy) ethanol. Other suitable surfactants include, for example, Alkyl Amine Ethoxylates; Alkyl Polyglucosides; Branched Secondary Alcohol Ethoxylates; Ethylene Oxide/Propylene Oxide Copolymers; Low Foam Surfactants; Nonylphenol Ethoxylates (NPE); Octylphenol Ethoxylates; Secondary Alcohol Ethoxylates and branched Secondary Alcohol Ethoxylates and Alkoxylates; Alkoxylates; Alkyldiphenyloxide Disulfonate Salts; Dioctyl Sulfosuccinates; Phosphate Esters; Sulfates, Polyether Sulfates, and Sulfonates; Phosphate Esters; Alkyldiphenyloxide Disulfonic acids and salts; chelating surfactants; n-Acyl-sarcosines/n-Acyl Sarcosinates; Ethylene Oxide/Propylene Oxide Copolymers; polyacrylates; anionic and nonionic surfactants; polyoxyethylene polyoxypropylene block copolymers; PLURONIC (BASF); sodium lauryl sulfate; TWEEN 20, which is a trademark of IC1 America; nonionic surfactants, such as a water soluble polyoxyethylene monoester of sorbitol with a $C_{10-18}$ fatty acid ester of sorbitol (and sorbitol anhydrides), consisting predominantly of the monoester, condensed with about 10-30, preferably about 20 moles of ethyleneoxide, the fatty acid (aliphatic hydrocarbon-monocarboxylic acid) may be saturated or unsaturated, e.g. lauric, palmitic, stearic, oleic acids. TWEEN 20 (which is a polyoxyethylene (20) sorbitan monolaurate); Anionic surfactants are also useful, such as water soluble salts of higher fatty acid monoglyceride monosulfates, as sodium salts of the monosulfated monoglycerides, or hydrogenated coconut oil fatty acids, higher alkyl-sulfates, such as sodium lauryl sulfate and alkyl aryl sulfonates, such as sodium dodecyl benzene sulfonate; and the like. Other surfactants, such as fluorinated surfactants, and surface tension reducing materials may also be incorporated within the compositions. Still other useful surfactants include egg albumin, sarcosinate surfactants, isethionate surfactants and taurate surfactants. Suitable optional surfactants are described more fully in U.S. Pat. No. 3,959, 458, May 25, 1976, to Agricola et al.; U.S. Pat. No. 3,937,807, Feb. 10, 1976, to Haefele; and U.S. Pat. No. 4,051,234, Sep. 27, 1988, to Gieske et al., all of which are hereby incorporated by reference herein for such disclosure.

The compatibilizing agent in the wetting agent includes at least one compound that solubilizes, suspends or otherwise distributes the surfactant within the wetting agent. The compatibilizing agent preferably volatilizes upon formation of the controlled hydrophilic film to increase the concentration per area of the surfactant along the surface. Suitable compatibilizing agents include, but are not limited to, ethyl alcohol (ethanol), $C_2$-$C_4$ alcohols, wherein said alcohols may be linear, branched and/or cyclic. Particularly suitable compatibilizing agents include ethyl alcohol, propyl alcohol (including its isomers n-propyl alcohol and isopropyl alcohol), butyl alcohol (including it isomers namely n-butyl alcohol, se-butyl alcohol, iso-butyl alcohol and t-butyl alcohol) and combinations thereof.

The film stabilizing agent in the wetting agent includes at least one compound that maintains the hydrophilicity of the controlled hydrophilic film for a clinically acceptable time, such as a time to apply an impression material. For example, the film stabilizing agent permits the controlled hydrophilic film to maintain its hydrophilicity for at least 3 minutes, or at least 5 minutes or at least 7 minutes or at least 10 minutes. Suitable film stabilizing agents include, but are not limited to, glycerin, glycerol, polyethylene glycol, (including polyethylene glycol 300), polyvinyl alcohol, polypropylene glycol, copolymers of polyethylene, polypropylene glycol copolymer and combinations thereof. The film stabilizing agent is preferably soluble in the water in the wetting agent. While not wishing to be bound by theory or explanation, it is believed that the film stabilizing agent retains the water in the wetting agent in a manner that retains the water in the surface and permits a thickness, when brushed, that results in a controlled hydrophilic film.

It is preferred to include orally suitable compounds in the wetting agent, such as a water soluble or partially water soluble substance, such as water, glycerin, glycerol or a polyol or the like.

The wetting agent may also include other components, such as an additive including one or more of hemostatic, vasoconstrictor, anesthetic, desensitizing and flavoring agents. The material may also include thickening agents, diluents or fillers to modify the viscosity of the material as may be desired. Chemical initiators, accelerators, retardants or setting modifiers may also be added to the wetting agent to control the rate of setting reaction at the interface of the impression material and the dentition. It is also useful to include a colorant in the wetting agent to aid in determining its location on the dentition.

In delivering the wetting agent, the wetting agent is applied to the surface by brushing. Brushing includes applying the material to a surface using a brush, microbrush, applicator or similar device that applies the wetting agent to a surface. During the brushing process, a stream of air or similar process may optionally be used to displace excess or pooled material to promote a uniform film of suitable thickness.

It has been found that using a wetting agent as in the present invention, a lower film thickness may be achieved in the impression material. This allows the impression material to flow into sub-gingival parts of the preparation. Historically, capturing good sub-gingival detail is in part limited by the lack of flow of the impression material. The application of the pre-impression wetting agent, according to the present invention, would create a very hydrophilic surface that would enable a very hydrophilic impression material (such as Aquasil Ultra available from DENTSPLY International) or even somewhat hydrophilic material to flow easier into these difficult to reach sub-gingival places. Also if a dental clinician was able to achieve better impression material flow through the application of a surface treatment agent, excessive or substantially reduced gingival retraction is achievable. This substantially eliminates or reduces patient tissue trauma that can occur during the retraction process.

As an example, a wetting agent having 3 wt % of Igepal CO 520 was mixed with about 3 wt % of aluminum chloride (Hemogin-L from VanR) in an aqueous solution. The solution may be buffered or unbufferred. When applied to dentition prior to taking an impression, the dentition was wetted to the extent that an improved flow of the impression material onto dentition surfaces was observed. It is preferred to employ from about 0 to about 25 wt % of a homeostatic agent, such as aluminum chloride, aluminum sulfate or the like. It is also understood that other components, such as the homeostatic agent, may also provide a surface tension reducing effect, and hence may be employed in the present invention either with or as a substitute to traditional surfactants. Hence, any material that will reduce the surface tension by wetting the dentition is within the scope of the invention.

In one embodiment, the wetting agent includes from about 20 to about 40 wt % compatibilizing agent, from about 1 to about 5 wt % surfactant, from about 10 to about 25 wt % film stabilizing agent and balance essentially water. In another embodiment, the wetting agent includes from about 20 to about 40 wt % compatibilizing agent, from about 20 to about 30 wt % hemostatic agent, from about 1 to about 5 wt % surfactant, from about 10 to about 25 wt % film stabilizing agent and balance essentially water. Other additives may be included in an amount from about 0 to about 5 wt %.

Figure 2:
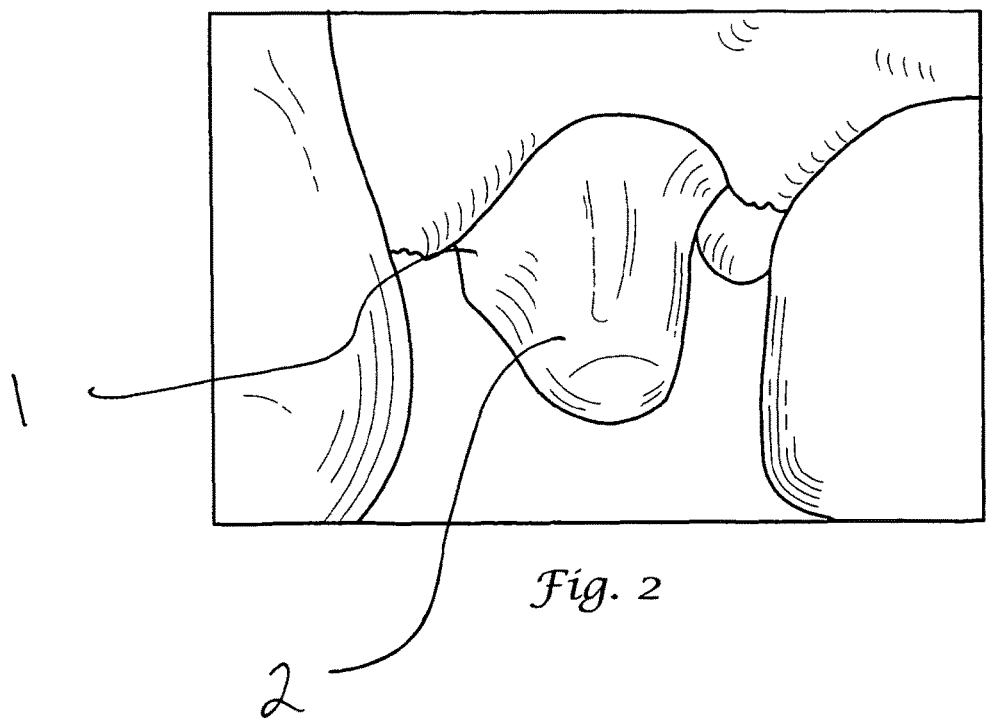
FIG. 2 is an elevational view of a prepared tooth having a wetting agent applied thereto, according to an embodiment of the present invention.

The wetting agent, as described above, was employed substantially immediately prior to the taking of a dental impression as follows. Following tooth (1 in FIG. 1) preparation and prior to taking the impression, the agent (2 in FIG. 2) is "painted" or otherwise applied onto the entire preparation in an isolated environment (usually with cotton rolls as is standard practice). Before the application of the impression material (such as, but not necessarily, a low viscosity material) the isolated preparation would be blown with a stream of air, thus leaving a very thin film of the surfactant based pre-impression surface agent on the tooth. The impression material applied to this surface will now flow freely on the surface. When the wetting agent also contains a hemostatic agent, commonly used gingival retraction cord can be soaked with the agent prior to placement using a standard single or double cord technique. If bleeding would occur during the placement of the cords, the packed preparations would be rinsed free of all blood and saliva, isolated properly and then the agent would be re-applied to the entire surface of the preparation as well as the placed cords. The impression process would then follow by the removal of the cord, application of a stream of air, and then syringing of the impression material on the preparation with the thin film.

Figure 3:
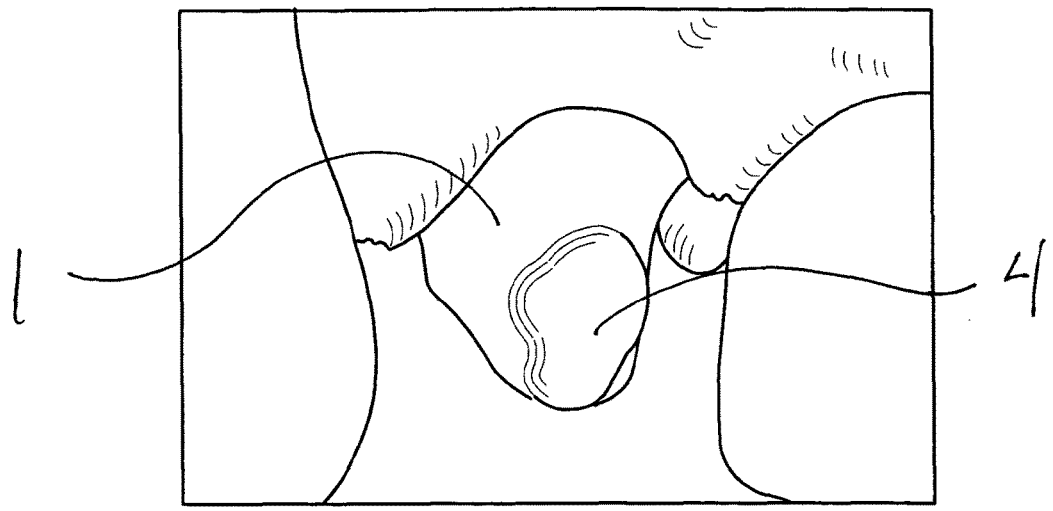
FIG. 3 is an elevational view of a prepared tooth having impression material applied without the inventive wetting agent.
Figure 4:
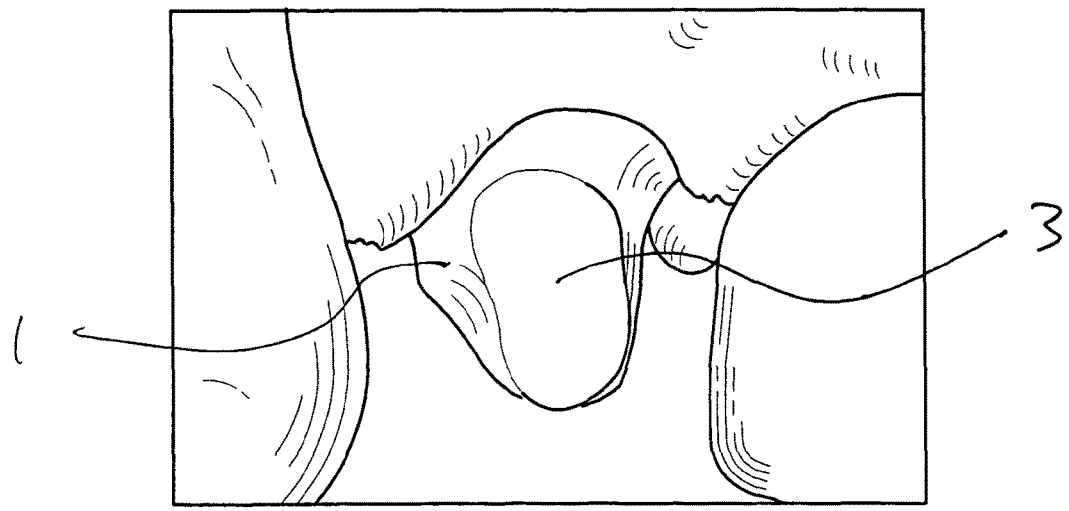
FIG. 4 is an elevational view of a prepared tooth having impression material applied with the inventive wetting agent, according to an embodiment of the present invention.

As a comparison, a dental impression was made using the same impression material but without the step of first conditioning the dentition with the wetting agent, according to the present disclosure. When compared, the impression 3 made according to the present invention (FIG. 4) showed more improved impression material flow than the material 4 applied without the inventive wetting agent (FIG. 3). If a hydrophilic material is placed on dry surface, the benefit of the hydrophilic impression material is limited. However, if a controlled hydrophilic film is applied to the tooth and preferably employing the same surfactant as may be present in the impression material itself, "like" surfaces would permit greater flow.

The wetting material, according to the invention, may also include additives, such as flavorants, scenting agents, viscosity modifiers, preservatives, antioxidants, coloring agents, and the like.

It is apparent therefore, that the inventive use of a wetting agent when taking a dental impression improves the adaptation of the impression material to the dentition. The invention has been described herein without attempting to describe all of the embodiments thereof as may be within the scope of the invention and included variations will be apparent to those skilled in the art. The scope of the invention shall be determined only by any attached claims.

What is claimed is:

1. A method of taking a dental impression comprising the steps of:
    conditioning a surface comprising one or more of a dentition and a dental appliance by the application thereto of a wetting agent to form a controlled hydrophilic wet film, the wetting agent comprising:
        water;
        a surfactant;
        a compatibilizing agent; and
        a film stabilizing agent;
    wherein the controlled hydrophilic wet film is hydrophilic and is formed by brushing the wetting agent onto the one or more of dentition and dental appliance, the brushing controlling a thickness and hydrophilicity of the controlled hydrophilic wet film to a thickness and hydrophilicity that is capable of inducing flow of an impression material that comes into contact with the controlled hydrophilic wet film, the flow being sufficient to flow into sub-gingival places;
    contacting the controlled hydrophilic wet film on the one or more of dentition and dental appliance with a dental impression material selected from the group consisting of hydrophilic and hydrophobic dental impression materials.

2. The method of claim 1, wherein the film stabilizing agent comprises a compound selected from the group consisting of glycerin, glycerol, polyethylene glycol, polyvinyl alcohol, polypropylene glycol, copolymers of polyethylene, polypropylene glycol copolymer and combinations thereof.

3. The method of claim 2, wherein the film stabilizing agent comprises glycerin.

4. The method of claim 2, wherein the film stabilizing agent comprises polyethylene glycol.

5. The method of claim 1, wherein the surfactant is a nonyl phenoxy-poly (ethyleneoxy) ethanol.

6. The method of claim 1, wherein the compatibilizing agent comprises a compound selected from the group consisting of ethyl alcohol, propyl alcohol, butyl alcohol and combinations thereof.

7. The method of claim 1, wherein the compatibilizing agent comprises ethyl alcohol.

8. The method of claim 1, wherein the dental impression material is a vinyl polysiloxane material.

9. The method of claim 1, wherein the impression material is an elastomer.

10. The method of claim 1, wherein the impression material is an alginate or hydrocolloid based impression material.

11. The method of claim 1, wherein the surface comprises the surface of a dental appliance.

12. The method of claim 1, wherein the surfactant is the same as a surfactant present in the impression material.

13. The method of claim 1, wherein the wetting agent includes about 3 wt % surfactant.

14. The method of claim 1, wherein the wetting agent includes from about 20 to about 40 wt % compatibilizing agent, from about 1 to about 5 wt % surfactant, and from about 10 to about 25 wt % film stabilizing agent, and water.

15. The method of claim 1, wherein the wetting agent further includes a hemostatic agent.

16. The method of claim 15, wherein the hemostatic agent comprises aluminum chloride or aluminum sulfate.

17. The method of claim 1, wherein the wetting agent includes an additive selected from the group consisting of hemostatic, vasoconstrictor, anesthetic, desensitizing and flavoring agents.

18. The method of claim 1, wherein the wetting agent includes from about 20 to about 40 wt % compatibilizing agent, from about 20 to about 30 wt % hemostatic agent, from about 1 to about 5 wt % surfactant, from about 10 to about 25 wt % film stabilizing agent, and water.

19. The method of claim 1, wherein the wetting agent and impression material flows into a sub-gingival portion of the dentition.

20. A method of taking a dental impression comprising the steps of:
    conditioning a surface comprising one or more of a dentition and a dental appliance by the application thereto of a wetting agent to form a controlled hydrophilic wet film, wherein the controlled hydrophilic wet film is formed by brushing the wetting agent onto the one or more of dentition and dental appliance, the brushing controlling a thickness and hydrophilicity of the controlled hydrophilic wet film to a thickness and hydrophilicity that is capable of inducing flow of an impression material that comes into contact with the controlled hydrophilic wet film, the flow being sufficient to flow into sub-gingival places;
    contacting the controlled hydrophilic wet film on the one or more of dentition and dental appliance with a dental impression material selected from the group consisting of hydrophilic and hydrophobic dental impression materials; and
    wherein said wetting agent comprises a surfactant and a carrier;
    wherein the carrier is a water soluble composition comprising glycerin; and
    wherein the conditioning comprises rendering the surface of the one or more of dentition and dental appliance surface hydrophilic.

21. A method of taking a dental impression comprising the steps of:

conditioning a surface comprising one or more of dentition and dental appliance by the application thereto of a wetting agent to form a controlled hydrophilic wet film, wherein the controlled hydrophilic wet film is formed by brushing the wetting agent onto the one or more of dentition and dental appliance, the brushing controlling a thickness and hydrophilicity of the controlled hydrophilic wet film to a thickness and hydrophilicity that is capable of inducing flow of an impression material that comes into contact with the controlled hydrophilic wet film, the flow being sufficient to flow into sub-gingival places;

contacting the controlled hydrophilic wet film on the one or more of dentition and dental appliance with a dental impression material selected from the group consisting of hydrophilic and hydrophobic dental impression materials; and wherein said wetting agent comprises a surfactant and a carrier;

wherein the carrier is a water soluble composition comprising polyethylene glycol; and wherein the conditioning comprises rendering the surface of the one or more of dentition and dental appliance surface hydrophilic.

22. A method of taking a dental impression comprising the steps of:

preparing a dentition with a wetting agent, the wetting agent comprising:

water;

a surfactant;

a compatibilizing agent; and a film stabilizing agent;

wherein the preparing includes conditioning the dentition by the application thereto of the wetting agent by one or both of a gingival retraction cord that has been contacted with the wetting agent and brushing with the wetting agent to form a controlled hydrophilic wet film, the conditioning controlling a thickness and hydrophilicity of the controlled hydrophilic wet film to a thickness and hydrophilicity that is capable of inducing flow of an impression material that comes into contact with the controlled hydrophilic wet film, the flow being sufficient to flow into sub-gingival places; and contacting the dentition with a dental impression material.

* * * * *